United States Patent [19]

Nichols et al.

[11] Patent Number: 5,474,679
[45] Date of Patent: Dec. 12, 1995

[54] FILTER FOR MEDICAL INSTRUMENT STERILIZATION CONTAINERS

[75] Inventors: Robert L. Nichols; William H. Patterson, both of Jacksonville, Tex.

[73] Assignee: Johnson & Johnson Medical, Inc., Arlington, Tex.

[21] Appl. No.: 87,845

[22] Filed: Jul. 1, 1993

Related U.S. Application Data

[63] Continuation of Ser. No. 980,506, Nov. 23, 1992, abandoned, which is a continuation of Ser. No. 664,030, Mar. 4, 1991, Pat. No. 5,227,074.

[51] Int. Cl.$^6$ ..................................................... B01D 29/05
[52] U.S. Cl. ............................. 210/477; 55/504; 55/511; 55/DIG. 31; 206/363; 206/438; 210/482; 210/484; 422/292; 422/310
[58] Field of Search ............................ 210/441, 451, 210/455, 470, 477, 482, 484, 485, 495, 497.2, 498, 499; 55/502, 504, 490, 511, DIG. 31; 422/101, 292, 297, 300, 310; 206/363, 438, 439; 99/295

[56] References Cited

U.S. PATENT DOCUMENTS

| | | | |
|---|---|---|---|
| 2,342,067 | 2/1944 | Turner. | |
| 2,727,650 | 12/1955 | Moynihan et al.. | |
| 2,784,843 | 3/1957 | Braunlich | 210/164 |
| 2,959,832 | 11/1960 | Baermann. | |
| 3,124,725 | 3/1964 | Leguillon. | |
| 3,410,395 | 11/1968 | Sellers. | |
| 3,437,423 | 4/1969 | Mondiadis. | |
| 3,454,189 | 7/1969 | Lauterbach. | |
| 3,480,145 | 11/1969 | Gladden | 210/223 |
| 3,697,223 | 10/1972 | Kovalcik et al.. | |
| 3,750,827 | 8/1973 | Wick. | |
| 3,831,759 | 8/1974 | Gelman et al. | 210/232 |
| 3,890,096 | 6/1975 | Nichol et al.. | |
| 3,946,872 | 3/1976 | Sturm | 206/525 |
| 4,105,407 | 8/1978 | Sanderson | 220/316 |
| 4,121,714 | 10/1978 | Daly et al. | 206/343 |
| 4,124,141 | 11/1978 | Armentrout et al. | 220/306 |
| 4,154,342 | 5/1979 | Wallace | 206/439 |
| 4,196,166 | 4/1980 | Sanderson et al. | 422/33 |
| 4,210,674 | 7/1980 | Mitchell | 436/107 |
| 4,251,482 | 2/1981 | Sanderson et al. | 422/26 |
| 4,267,420 | 5/1981 | Brastad | 219/10.55 F |
| 4,271,973 | 6/1981 | Quagliaro et al. | 220/371 |
| 4,331,067 | 5/1982 | Mysicka | 99/295 |
| 4,359,495 | 11/1982 | Schroeder et al. | 428/458 |
| 4,372,921 | 2/1983 | Sanderson et al. | 422/300 |
| 4,396,583 | 8/1983 | LeBoeuf | 422/301 |
| 4,402,407 | 9/1983 | Maly | 422/300 |
| 4,416,417 | 11/1983 | Sanderson et al. | 236/92 R |
| 4,416,906 | 11/1983 | Watkins | 219/10.55 E |
| 4,457,327 | 7/1984 | Pepper | 422/112 |
| 4,458,705 | 7/1984 | Cawood | 422/300 |
| 4,468,321 | 8/1984 | St. John | 210/482 |
| 4,512,498 | 4/1985 | Leibinger | 220/371 |

(List continued on next page.)

FOREIGN PATENT DOCUMENTS

| | | |
|---|---|---|
| 152544 | 11/1984 | European Pat. Off.. |
| 2542200 | 9/1984 | France. |
| 2839219 | 3/1980 | Germany. |
| 2165754 | 4/1986 | United Kingdom. |

OTHER PUBLICATIONS

Kirk–Othmer, *Encyclopedia of Chemical Technology*, 3rd Ed., vol. 5, "Castor Oil to Chlorosulfuric Acid", pp. 251–253.

*Primary Examiner*—John Kim
*Attorney, Agent, or Firm*—Baker & Botts

[57] ABSTRACT

A filter (32) is provided for a medical sterilization container (10) having a port (18,22,24) allowing fluid communication between the interior of container (10) and the surrounding environment. A peripheral frame (44) is adapted to cooperate with the port (18,22,24). A plurality of cross-members (54) span an aperture (48) formed by a frame (44). A filter medium (58) is disposed across the aperture (48) so as to be interposed between the interior of the container and the cross-members (54).

3 Claims, 2 Drawing Sheets

U.S. PATENT DOCUMENTS

| | | | |
|---|---|---|---|
| 4,551,311 | 11/1985 | Lorenz | 422/300 |
| 4,584,182 | 4/1986 | Sanderson et al. | 422/310 |
| 4,617,178 | 10/1986 | Nichols | 422/310 |
| 4,704,254 | 11/1987 | Nichols | 422/310 |
| 4,716,025 | 12/1987 | Nichols | 422/310 |
| 4,728,504 | 3/1988 | Nichols | 422/310 |
| 4,732,187 | 3/1988 | Mönch | 422/300 |
| 4,748,003 | 5/1988 | Riley | 422/112 |
| 4,783,321 | 11/1988 | Spence | 422/300 |
| 4,859,348 | 8/1989 | Jusaitis et al. | 210/495 |
| 4,860,645 | 8/1989 | van der Lijn et al. | 210/482 |
| 4,900,519 | 2/1990 | Nichols | 422/292 |
| 4,915,918 | 4/1990 | Nichols | 422/300 |
| 5,028,328 | 7/1991 | Long | 210/477 |
| 5,080,874 | 1/1992 | Nichols | 206/363 |

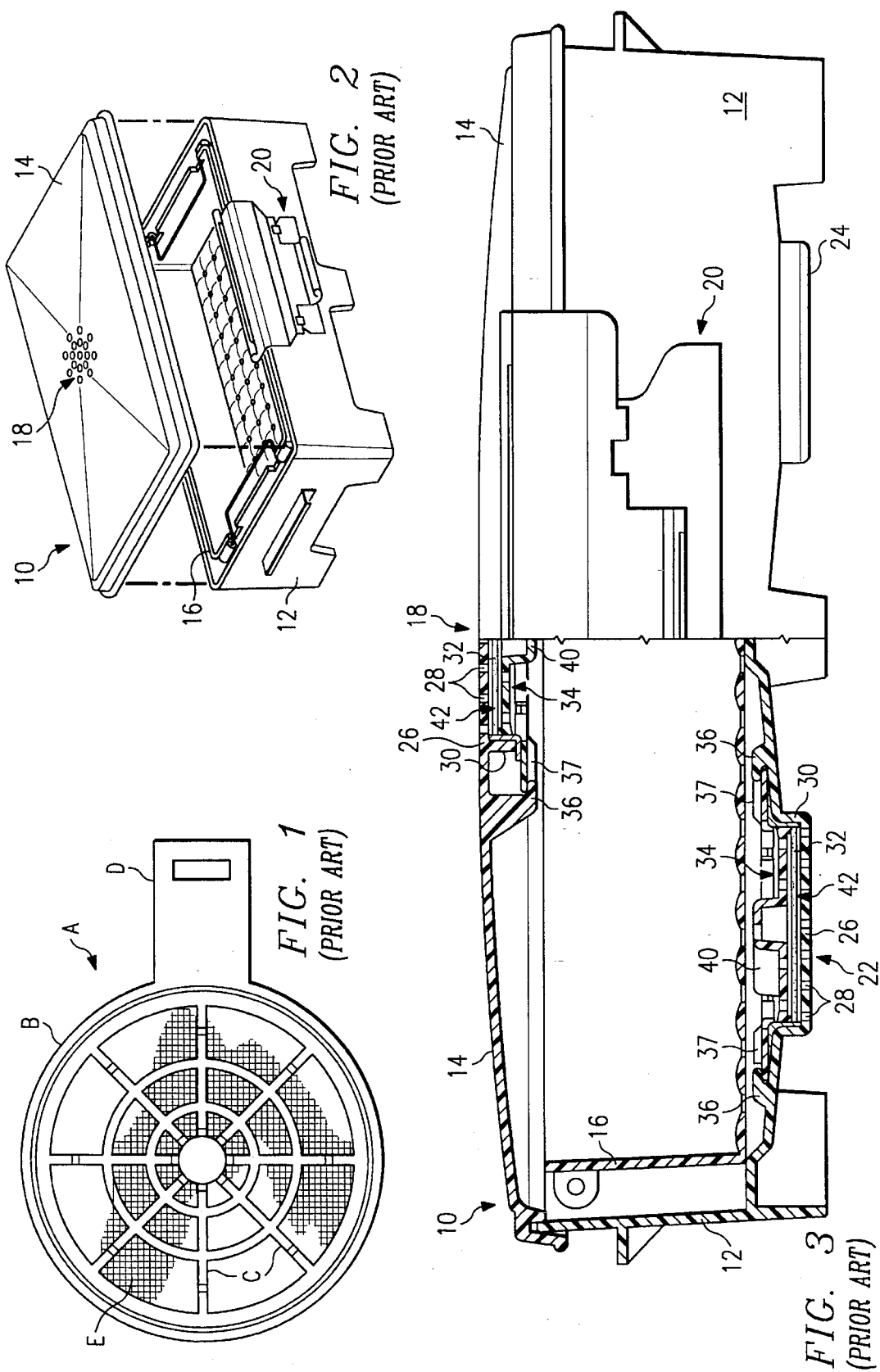

FILTER FOR MEDICAL INSTRUMENT STERILIZATION CONTAINERS

CROSS REFERENCE TO RELATED APPLICATIONS

This application is a continuation of application Ser. No. 07/980,506 filed Nov. 23, 1992, by Robert L. Nichols and William H. Patterson, entitled "Filter for Medical Instrument Sterilization Containers" now abandoned, which was a continuation of application Ser. No. 07/664,030 filed Mar. 4, 1991, by Robert L. Nichols and William H. Patterson, now U.S. Pat. No. 5,227,074, issued Jul. 13, 1993.

TECHNICAL FIELD OF THE INVENTION

The present invention relates in general to medical instrument sterilization containers and more particularly to an improved filter for medical instrument sterilization containers.

BACKGROUND OF THE INVENTION

It is common practice in hospitals and other medical environments to sterilize medical instruments with steam or other sterilizing gases. Sterilization containers provide a convenient enclosure in which the sterilization can be performed. These containers normally have housings with a bottom and sidewalls, removable lids, ports for the passage of sterilization gases and condensate, and a sealing mechanism to prevent contaminants from entering the container after sterilizing. The containers may have one or more inlet ports in the lid and one or more outlet ports in the bottom. A filter unit, having anyone of a number of commercially available filter mediums which allow the passage of air, steam and other sterilization gases but which prevent, retard or inhibit, the passage of contaminants such as dirt, dust and bacteria, is normally disposed in each of the ports. The filter mediums are most commonly hydrophobic like, such that moisture will not pass therethrough unless a sufficient pressure difference is created between the inside of the medical sterilization container and the surrounding sterilizing chamber.

During steam sterilization processes, steam is forced through the various ports in the container to sterilize microorganisms such as bacteria. During this process, water condensate is normally left behind. Although the bacteria inside the container should be substantially eliminated through the sterilization process, medical technicians are trained to regard moisture as a breeding place for bacteria, and thus condensate tends to cause technician acceptance problems as well as providing an actual possible breeding ground for bacteria. In addition, the condensate increases the possibility for rusting and other deterioration of the medical instruments in the container.

Steam sterilization units, whether they be gravity steam, pulsating, pressure steam or alternating vacuum and pressure or the like, all normally have a drying cycle. During the drying cycle, the pressure of the chamber surrounding the medical sterilization container is normally decreased in order to lower the boiling point of the moisture.

Presently available filter units normally consist of a frame which supports a filter element across the aperture of the corresponding port. One or more cross-members may be provided across the frame for strength and rigidity. These cross-members, while strengthening the filter unit, can reduce the efficiency of the drying cycle. This is due to the fact that the cross-members in the presently available filter units have been interposed between the interior of the medical sterilization container and the filter medium when the filter unit is seated in a filter port. The cross-members thereby provide an internal surface area which can impede condensate and steam which is exiting the port of the container. Further, the cross-members provide an undesirable area on which steam can recondense during the drying process, further impeding drainage of condensate from the container. The overall result is an unnecessarily lengthy drying process.

Thus, the need has arisen for a filter unit which enables the unimpeded flow of moisture out of a medical instrument sterilization container port during a drying cycle. This will allow faster and more efficient sterilization while reducing the chances of rejection of the sterilized instruments by inspecting medical technicians. Such a filter unit, however, would retain the necessary strength and rigidity to keep the filter unit firmly seated in the associated filter port.

SUMMARY OF THE INVENTION

According to the present invention, a filter is provided for a medical sterilization container having a port allowing fluid communication between the container interior and the surrounding environment. The filter includes a peripheral frame which is adapted to cooperate with the port. A plurality of cross-members span an aperture formed by the peripheral frame. A filter medium is disposed across the aperture so as to be interposed between the interior of the container and the cross-members.

According to other aspects of the invention, a sidewall extends from the peripheral edge of the frame to a lip. The sidewall extends at an angle to enable the filter to cooperate with the sidewalls of the corresponding port, creating a seal therebetween.

The present invention provides significant technical advantages over currently available filters for medical sterilization containers. By having the filter medium disposed between the interior of the container and the cross-members, the flow of moisture and condensate out of the medical sterilization container is not impeded. The moisture does not encounter the surface area of the cross-members until it has crossed the protective barrier provided by the filter medium. The filter, however, retains the advantages of the cross-members which provide the necessary strength and rigidity to keep the filter unit firmly engaged with the filter port.

BRIEF DESCRIPTION OF THE DRAWINGS

Other aspects of the invention and their advantages will be discerned when one refers to the following detailed description as taken in conjunction with the drawings, in which like numbers identify like parts, and in which:

FIG. 1 is a top view of a prior art filter;

FIG. 2 is a perspective view of medical instrument sterilization container;

FIG. 3 is a partial sectional view of the sterilization container of FIG. 2;

DETAILED DESCRIPTION OF THE INVENTION

Figure 4:
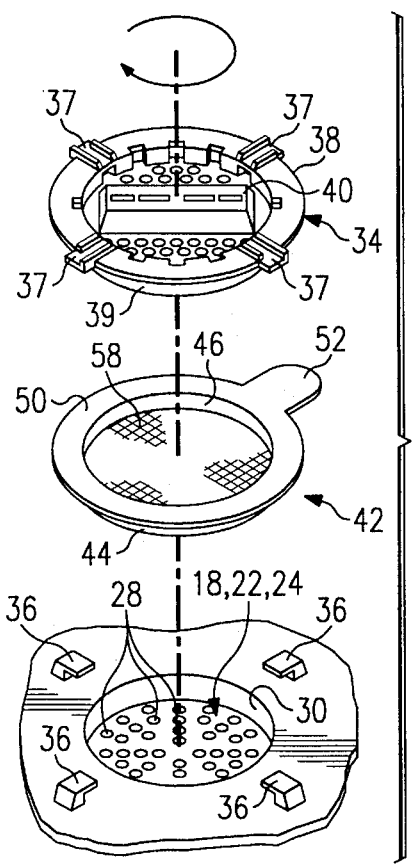
FIG. 4 is an exploded view of a selected filter port of the medical instrument sterilization container of FIGS. 2 and 3 and the improved filter and the associated retaining cover.

Preferred embodiments of the present invention are best understood by referring to FIGS. 1–5 of the drawings, like numerals being used for like and corresponding parts of the various drawings.

A top view of a currently available filter unit is shown in FIG. 1, and includes a plastic member A having a lip B, plastic cross-members C and a tab D extending from lip B to allow manual insertion and removal from a filter port. A hydrophobic like filter medium E is disposed across the aperture formed by plastic member A to prevent, retard or inhibit the passage of contaminants. A representative prior art filter unit is produced by Monarch Products, Inc., under part number 21030.

Referring first to FIG. 2, a prior art medical sterilization container is shown generally at 10, and includes the housing 12 and a removable lid 14. Typical medical sterilization containers are disclosed in U.S. Pat. Nos. 4,617,178; 4,752,453; 4,728,504; 4,900,519 and 4,915,918, all issued to Nichols. Lid 14 is preferably domed-shaped as shown in FIG. 1, however, lid 14 may also have other configurations as known in the art, such as being substantially flat. Removable tray 16 is received within the housing 12 and is adapted to receive various medical instruments, such as knives, scissors and the like.

An inlet port 18 is disposed through lid 14 in order to allow the passage of sterilizing steam and gases therethrough, while preventing, retarding or inhibiting the passage of bacteria or other contaminants such as dirt and dust into the interior of the container. Two additional outlet ports, to be discussed below, are disposed in the bottom of housing 12. Metal clamps 20 are attached to both sides of the housing 12 and are manually movable to clamp against the side of the lid 14 in order to lock lid 14 to housing 12. Suitable sealing surfaces are provided between the housing 12 and the lid 14 creating an essentially sealed container when the lid 14 is clamped to housing 12.

FIG. 3 is a partially sectioned view of sterilization container 10, which depicts outlet ports 22 and 24 extending from the bottom of housing 12. Ports 18, 22 and 24 each include a circular base 26 having a plurality of apertures 28 which communicate with the surrounding atmosphere. In inlet port 18, base 26 is an integral part of domed shaped lid 14. Annular sidewalls 30 form a receptacle which is adapted to receive an improved removable filter unit 32 according to the invention, discussed in detail below. Removable filter unit 32 is held tightly within annular sidewalls 30 by a twistable cover 34 which engages a plurality of locking members 36 disposed around the periphery of the respective port. The sidewalls 46 extend at an angle to enable the filter to cooperate with the sidewalls 30 of the corresponding port, creating a seal therebetween.

Referring next to FIG. 4, an exploded view is shown which demonstrates the cooperation between a selected port 18, 22 or 24 with an improved filter unit 32 and twistable cover 34. Twistable cover 34 includes four locking flanges 37 which extend from a lip member 38 extending from an outer sidewall 39. Locking flanges 37 are positioned to be rotated into locking members 36 formed around the periphery of the respective port 18, 22 or 24. A gripping member or handle 40 is provided on twistable cap 34 to facilitate its rotation within the respective annular sidewalls 30.

Figure 5A:
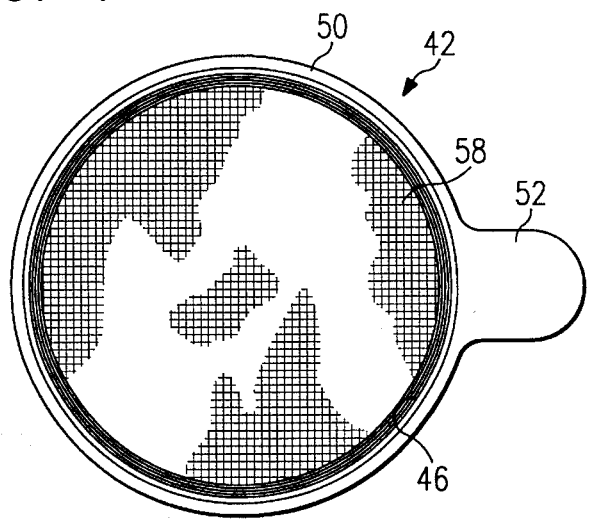
FIGS. 5a–5c are respective top, side and bottom views of an improved filter in accordance with the present invention.
Figure 5B:
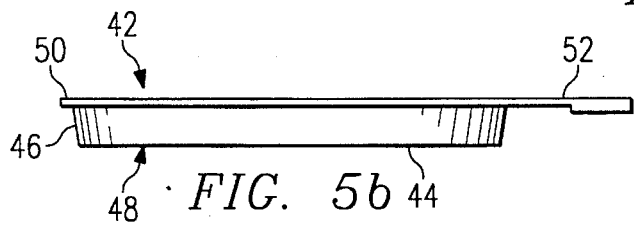
Figure 5C:
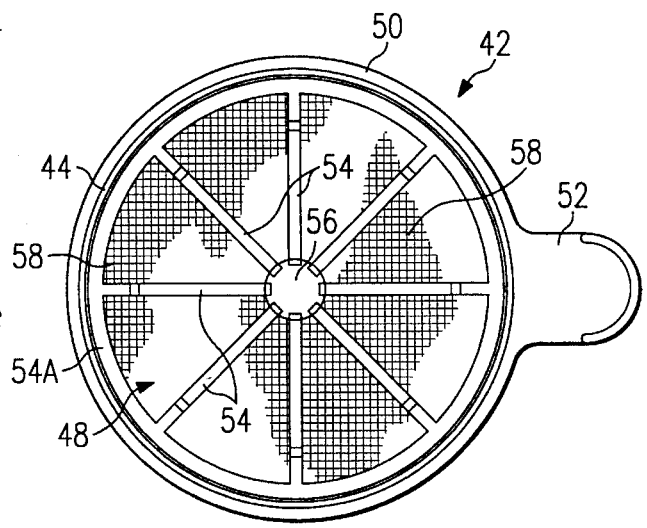

FIGS. 5a–c are respective top, side and bottom views of an improved filter unit 32 according to the invention. Filter unit 32 includes a circular plastic member 42 having an annular frame 44 and sidewalls 46 forming an aperture 48. Plastic member 42 preferably is semiflexible for ease of insertion into the filter port and such that a tight fit in the port is realized when pressure is applied by twistable cover 34. In a preferred embodiment, plastic member 42 is formed of propylene, however the present invention is not limited thereto, and may be constructed of any material resistant to heat and sterilizing gases. Sidewalls 46 extend at an angle from the periphery of frame 44 such that a proper fit is achieved when filter unit 32 is inserted within sidewalls 30 of a corresponding filter port. A lip 50 extends outwardly from the edge of sidewalls 46 and is designed to seat on the area housing 12 immediately adjacent the port when filter unit 32 is in place. Tab 52 is provided to aid in the insertion into and removal from the selected port 18, 22 or 24.

A plurality of cross-members 54 extend inward from a plurality of points around the bottom of the annular frame 44 to give filter unit 32 rigidity and strength. Cross-members 54 may extend radially across annular frame 44 in a spoke-like fashion from a nave 56 in preferred embodiments of the invention. A lower lip 54A is shown circumscribing the nave 56 adjacent to the outward ends of the cross-members 54. Filter medium 58 is disposed across cross-members 54 to cover aperture 48 created within the circumference of annular frame 44. Filter medium 58 may be non-woven polyolefin material or any one of the commercially available filter mediums which allow the passage of air or sterilants therethrough but which prevent, inhibit, or retard the passage of contaminants, such as dirt, dust, bacteria and the like. Typically, filter medium 58 will be hydrophobic like. It is important to note that filter medium 58 covers cross-members 54 such that the filter medium 58 stands between the interior of the medical sterilization container 10 with which the filter unit 32 is being employed, and cross-members 54.

During the drying cycle, the present invention eliminates the problem of having the cross-members 54 impeding the exit of condensate, steam and sterilizing gases from the interior of medical instrument sterilization 10. With the present invention, moisture is first drawn out of the sterilization container 10 through filter medium 58 before encountering cross-members 54. In other words, filter medium 58 is disposed upstream of the fluid flow, while cross-members 54 are disposed down-stream of the fluid flow. This improves the efficiency of the sterilization cycle, by reducing the amount of drying time required. At the same time, cross-members 54 are still available to provide strength and rigidity to the filter unit 32. A further advantage is realized in having the cross-members downstream of the fluid flow: additional support is rendered against the vacuum pressure being exerted on the filter medium 58 while the moisture and condensate is being drawn out.

Thus, the present invention provides significant advantages over the existing filter units which employ cross-members for strength, but which impede the flow of moisture out of the sterilization container. The condensate has already passed the protective barrier of filter medium 58 before encountering the surfaces of the cross-members 54. At the same time, the cross-members 54 are still available to strengthen the filter unit, and even provide the further advantage of helping support the filter medium while pressure is being applied.

While preferred embodiments of the invention and its advantages have been set forth in the above-detailed description, the invention is not limited thereto, but only by the scope and spirit of the appended claims.

What is claimed is:

1. An apparatus for sterilizing medical instruments, the apparatus comprising:

a medical instrument sterilization container having a port allowing fluid communication between said container and surrounding environment; and a filter unit comprising:

a frame having side walls adapted to be received in said port of said medical instrument sterilization container so that a seal is realized between said port and said frame;

at least one cross-member spanning an aperture formed by said frame; and a filter medium disposed across said aperture for being interposed between said interior of said container and said cross-members when said frame is received in said port.

2. A filter for a medical sterilization container having a port allowing passage of sterilizing steam or gases between the interior of said container and the surrounding environment, said port having sidewalls for receiving said filter, said filter comprising:

an angled sidewall defining an aperture with an upper and a lower opening, the upper opening having a larger diameter than the lower opening;

an upper lip, extending radially outwardly from the upper opening of said aperture, adapted to seat upon said container adjacent to said port, said lip in combination with said angled sidewall creating a seal between said port and said filter;

at least one cross member attached to the filter and spanning the lower opening of said aperture;

a lower lip adjacent said cross member and extending radially inward from the lower opening; and a hydrophobic, permeable filter medium disposed across said lower opening, and supported by said cross member and said lower lip so that the filter medium is interposed between the interior of said container and said cross member.

3. A system for sterilizing medical instruments, comprising:

a medical instrument sterilization container having a port allowing fluid communication between an interior of said container and a surrounding environment; and a filter unit comprising:

an angled sidewall defining an aperture with an upper and a lower opening, the upper opening having a larger diameter than the lower opening;

a lip extending radially outwardly from the upper opening of said aperture adapted to seat upon an area of said container surrounding said port, said lip in combination with said sidewall adapted to create a seal between said port and said filter;

at least one cross member spanning the lower opening of said aperture; and a filter medium disposed across the lower opening of said aperture and supported by said cross member so that the filter medium is interposed between the interior of said container and said cross member.

* * * * *